United States Patent [19]

Wilk

[11] Patent Number: 5,232,440
[45] Date of Patent: Aug. 3, 1993

[54] METHOD AND DEVICE FOR DRAINING ABSCESS

[76] Inventor: Peter J. Wilk, 185 West End Ave., New York, N.Y. 10023

[21] Appl. No.: 841,802

[22] Filed: Feb. 26, 1992

[51] Int. Cl.$^5$ ............................................. A61M 31/00
[52] U.S. Cl. ..................... 604/49; 604/104; 604/165; 604/174; 604/281
[58] Field of Search ............ 604/27, 28, 48, 49, 604/73, 93, 104–106, 158, 161, 164–165, 264, 278, 281, 174, 175, 166

[56] References Cited

U.S. PATENT DOCUMENTS

| | | | |
|---|---|---|---|
| 4,154,242 | 5/1979 | Termanini | 604/105 |
| 4,441,495 | 4/1984 | Hicswa . | |
| 4,593,687 | 6/1986 | Gray et al. | 604/104 |
| 4,638,803 | 1/1987 | Rand . | |
| 4,699,611 | 10/1987 | Bowden | 604/51 |
| 4,737,141 | 4/1988 | Spits | 604/28 |
| 4,834,725 | 5/1989 | Iwatschenko | 604/281 |
| 4,986,810 | 1/1991 | Semrad | 604/106 |
| 4,986,814 | 1/1991 | Burney et al. | 604/164 |
| 5,112,310 | 5/1992 | Grobe | 604/175 |
| 5,122,122 | 6/1992 | Allgood | 604/174 |

FOREIGN PATENT DOCUMENTS 2659440 7/1977 Fed. Rep. of Germany .
3837779 5/1989 Fed. Rep. of Germany .

*Primary Examiner*—C. Fred Rosenbaum
*Assistant Examiner*—Corrine Maglione
*Attorney, Agent, or Firm*—R. Neil Sudol; Henry D. Coleman

[57] ABSTRACT

An assembly for use in drainage of an abscess comprises an outer tubular member provided in a distal end portion with a plurality of longitudinal slits. The distal end portion of the tubular member has a spring bias tending to form the distal end portion into a substantially spherical expanded configuration to anchor the distal end portion of the tubular member in an abscess. An inner tubular member or obturator is inserted into the outer tubular member and has a distal end provided with a cutting edge projecting from the outer tubular member. Locking components on the obturator and the outer tubular member serve to maintain the latter in a stretched out cylindrical configuration enabling insertion of the distal end portion into an abscess.

14 Claims, 2 Drawing Sheets

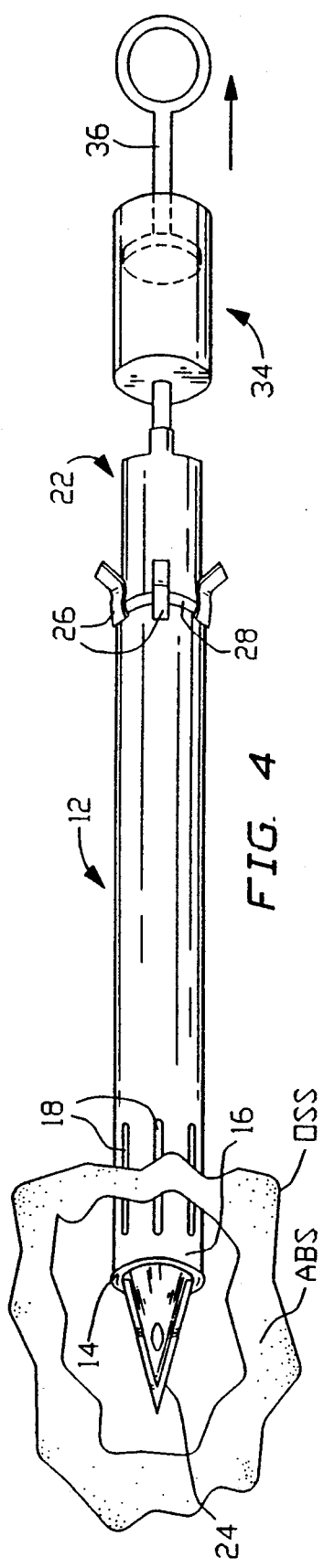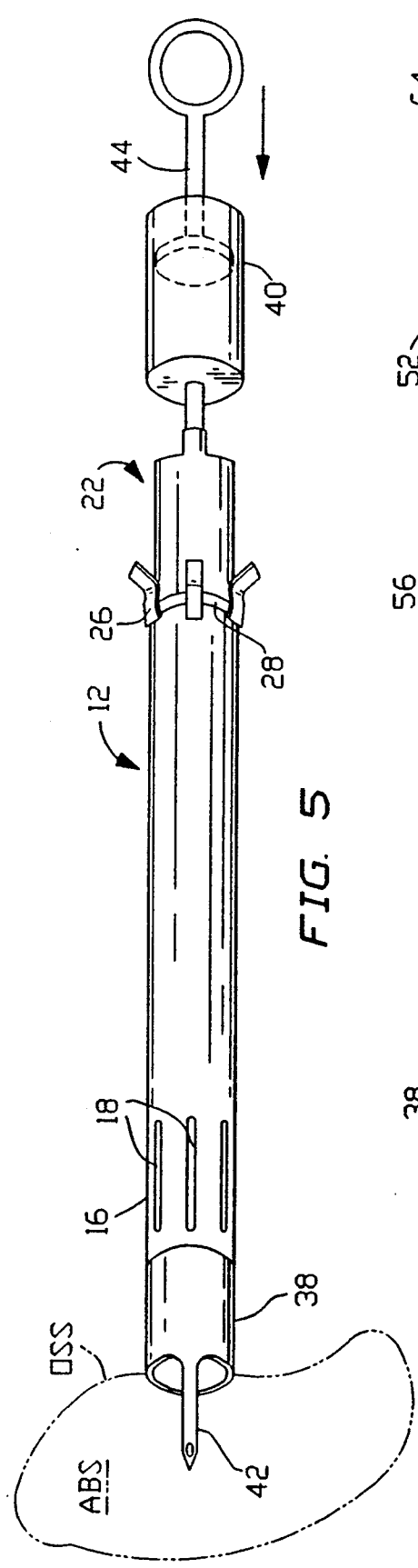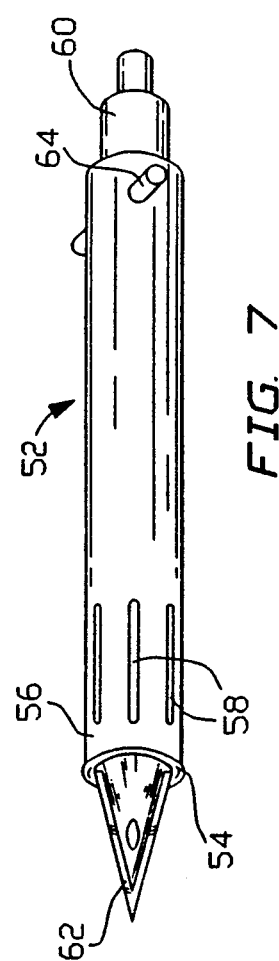

METHOD AND DEVICE FOR DRAINING ABSCESS

BACKGROUND OF THE INVENTION

This invention relates to an assembly or device for use in draining an abscess. This invention also relates to an associated method using the device.

An abscess is a collection of pus in infected tissue and is often accompanied by inflammation or swelling. To relieve the swelling, a surgeon makes an incision through skin tissues overlying the abscess. Although some pus may be removed immediately from the abscess to reduce the swelling, fluidic matter will continue to accumulate and swelling will recur unless measures are taken to ensure continued drainage from the infected tissues.

One procedure for ensuring continued drainage of an abscess involves the use of a tubular member which is closed at a distal end, i.e., the end which is inserted by the surgeon into the abscess. Along a distal portion proximal of the closed distal tip of the tube are provided a plurality of longitudinal slits. The tube is formed at its perforated distal portion with a spring bias tending to form that portion of the tube into a substantially spherical expanded anchoring configuration wherein the slits are opened.

To insert the distal end portion of the tube into the abscess, a rod is inserted into the tube. The tube is stretched so that the distal end portion thereof assumes an elongate cylindrical configuration, rather than a spherical or expanded configuration, thereby facilitating insertion of the tube through the incision in the skin tissues overlying the abscess. Upon insertion of the distal end portion of the tube into the abscess, the tube is released so that the distal end portion assumes the spherical or expanded configuration and opens the slots to enable or facilitate continued drainage of the pus or fluidic material from the abscess.

OBJECTS OF THE INVENTION

An object of the present invention is to provide an improved method for draining an abscess.

Another object of the present invention is to provide a device or assembly which is utilizable in the improved method.

Another, more particular, object of the present invention is to provide a device and a related method wherein a surgical procedure to drain an abscess is facilitated.

A further particular object of the present invention is to provide a device and a related method wherein a surgical procedure to drain an abscess has fewer steps than the above-described conventional procedure.

SUMMARY OF THE INVENTION

A device for use in draining an abscess comprises, in accordance with the present invention, an outer tubular member and an obturator inserted into the outer tubular member. The obturator has a distal end projecting from the tubular member, the distal end of the obturator being provided with a cutting edge. The tubular member is at least partially flexible.

Pursuant to another feature of the present invention, the tubular member has, at its distal end, a spring bias tending to form a distal end portion of the tubular member into an expanded configuration to anchor the tubular member in an abscess.

According to another feature of the present invention, a locking component is provided for releasably locking the obturator to the tubular member. This feature is particularly useful to stretch the tubular member over the obturator. The tubular member is thus maintained in a cylindrical configuration to facilitate insertion into an abscess.

The locking component or components may include an annular shoulder provided proximally of the cutting edge on the obturator. A ring-shaped lip on the tubular member engages the shoulder on the obturator. A further locking component is provided at the proximal end of the obturator for latching onto the flexible tubular member and maintaining the tubular member in a stretched, pre-firing configuration.

Pursuant to another feature of the present invention, a radio-opaque strip is fastened to the tubular member to facilitate, for example, disposition of the tubular member in a deep abscess.

Pursuant to another feature of the present invention, the tubular member is provided in its distal end portion with a plurality of perforations preferably in the form of slits extending longitudinally along the tubular member. The slits are opened when the locking components are disengaged and the tubular member released so that the distal end portion assumes an expanded, e.g., spherical, configuration.

Pursuant to another feature of the present invention, the obturator is tubular, while the drainage device or assembly further comprises a syringe connected to the obturator at a proximal end thereof. The syringe may be used to withdraw a fluidic sample from a presumed abscess prior to deployment of the flexible outer tubular member. Alternatively, or additionally, another syringe may be used to inject an aliquot of local anaesthetic prior to piercing of the skin tissues with the cutting edge of the obturator. In that case, a needle may be removably attached to the distal end of the obturator, whereby an ejection stroke of the syringe ejects anaesthetic from the syringe through the obturator and out along the needle.

A method for draining an abscess comprises, in accordance with the present invention, the steps of (a) puncturing a skin surface with a sharp distal end of an obturator inserted inside a tubular member, (b) inserting a distal end portion of the tubular member and the obturator through the skin surface into an abscess, (c) withdrawing the obturator from the tubular member while maintaining the distal end portion of the tubular member in the abscess, and (d) draining fluid from the abscess through the tubular member.

Pursuant to another feature of the present invention, the method further includes the step of expanding a distal end portion of the tubular member to anchor the tubular member in the abscess. Where the tubular member is at least partially flexible and is locked in a stretched configuration to the obturator prior to the step of puncturing, this expasion step is implemented by unlocking the obturator from the tubular member prior to the step of withdrawing.

The step of unlocking may include the step of releasing a locking element at a proximal end of the obturator. The obturator may be provided proximally of a cutting edge with an annular shoulder, while the tubular member may be provided at its distal end with a ring-shaped lip engaging the shoulder. In that event, the step of unlocking the obturator and the tubular member from one another includes the step of disengaging the lip from the shoulder.

Where the obturator is a tubular member, the method further comprises the step of exerting a suction force on the obturator from a proximal end thereof prior to the step of withdrawing, to obtain a sample of fluidic material in the abscess.

Pursuant to another feature of the present invention, the method further comprises the step of monitoring the location of the tubular member in the abscess by detecting the location of a radio-opaque strip fastened to the tubular member.

Pursuant to yet another feature of the present invention, the method also comprises the step of injecting an anaesthetic through the obturator and along a needle attached to the distal end of the obturator.

BRIEF DESCRIPTION OF THE DRAWING

FIG. 4 is a schematic side perspective view of the tubular member, obturator and syringe of FIG. 2, showing the syringe in a partially loaded configuration and a distal end of the obturator in an abscess.

FIG. 5 is a schematic side perspective view of the tubular member and obturator of FIGS. 2 and 4, showing an anesthetic syringe and a needle mounted to the proximal end and the distal end, respectively, of the obturator.

FIG. 6 is a side elevational view of the needle member of FIG. 5.

FIG. 7 is a side elevational view, on a reduced scale, of another abscess drainage device in accordance with the present invention.

DETAILED DESCRIPTION

Figure 1:
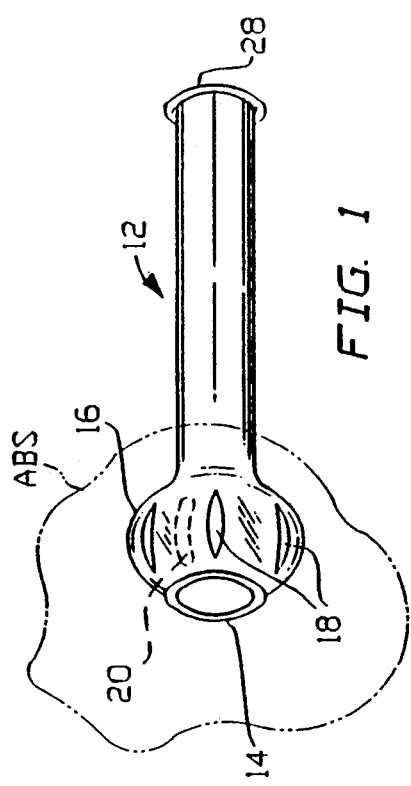
FIG. 1 is a schematic side perspective view of a flexible tubular member for use in an abscess drainage technique in accordance with the present invention, showing the tubular member with a distal end portion inserted in a substantially spherical configuration inside an abscess.

As illustrated in FIG. 1, a device for use in draining an abscess ABS comprises a tubular member 12 provided at a distal end with a ring-shaped lip 14 and further provided in a distal end portion 16 with plurality of perforations in the form of longitudinal slits 18. Distal end portion 16 is made of a flexible material with a spring bias tending to form the distal end portion into a substantially spherical expanded anchoring configuration, wherein slits 18 are opened, as shown in FIG. 1. Tubular abscess drainage member 12 may be provided with a radio-opaque strip 20 for facilitating a monitoring of the location of distal end portion 16 inside abscess ABS. Strip 20 can assume any shape or disposition which is effective for detection via X-ray equipment.

Figure 2:
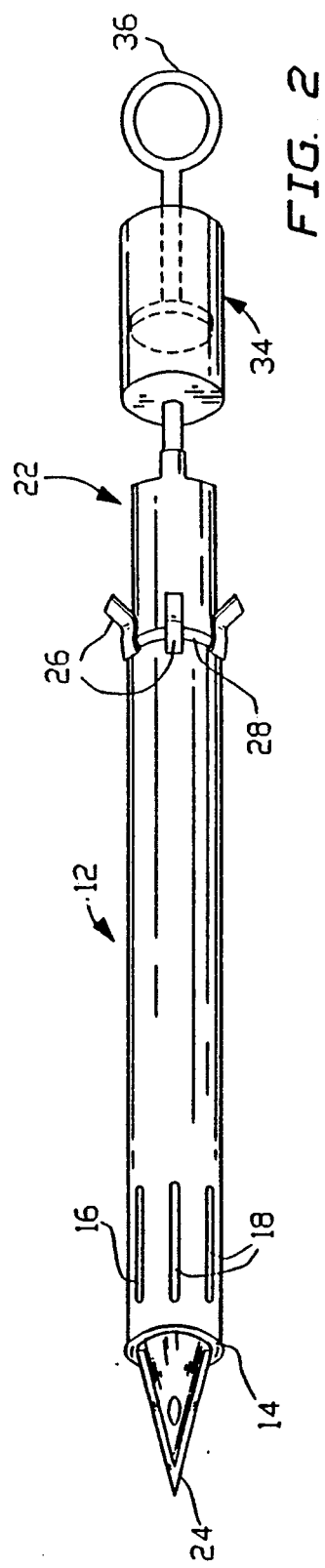
FIG. 2 is a schematic side perspective view of an abscess drainage assembly in accordance with the present invention, showing the flexible tubular member of FIG. 1 mounted or locked in a stetched cylindrical configuration to a tubular obturator and further showing a syringe in an unloaded pre-use configuration.

In order to dispose distal end portion 16 of tubular member 12 inside abscess ABS, a tubular obturator 22 is inserted into the tubular member 12, as illustrated in FIG. 2. Obturator 22 has a distal end provided with a cutting edge 24 which projects from tubular member 12 through an opening defined by ring-shaped lip 14.

Figure 3:
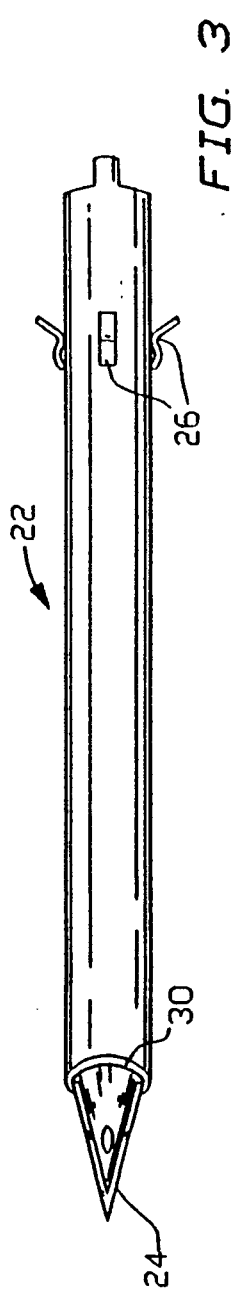
FIG. 3 is a schematic side perspective view of the tubular obturator of FIG. 2.

Prior to employment of the abscess drainage assembly illustrated in FIG. 2, tubular member 12 is locked in a stretched cylindrical configuration to obturator 22. To that end, a plurality of spring loaded locking components 26 are provided on the proximal end of obturator 22 for releasably latching onto an annular bead 28 at the proximal end of tubular member 12. Also for the purpose of temporarily locking tubular member 12 in the stretched cylindrical configuration to obturator 22, an annular shoulder 30 is provided proximally of cutting edge 24 on the obturator, as shown in FIG. 3. Ring-shaped lip 14 on tubular member 12 engages shoulder 30 to cooperate therewith and with locking components 26 to maintain tubular member 12 in the stretched cylindrical configuration.

As illustrated in FIG. 2, a syringe 34 is connected to obturator 22 at a proximal end thereof for removing a sample of fluidic material from abscess ABS. FIG. 4 shows a part of distal end portion 16 inserted into abscess ABS upon a piercing or puncturing of an overlying skin surface OSS with cutting edge 24. Upon insertion of cutting edge 24 into abscess ABS, a plunger member 36 of syringe 34 may be pulled back to apply a suction force to obturator 22, thereby drawing fluidic material from abscess ABS through the obturator 22.

If, upon obtaining a fluidic sample in syringe 34, a surgeon determines that a proper location in the abscess ABS has been found, obturator 22 is pushed further in the distal direction so that the entire distal end portion 16 of tubular member 12 is inside abscess ABS. Then, locking components 26 are actuated to release bead 28, whereupon distal end portion 16 assumes the spherical anchoring shape shown in FIG. 1 and whereupon obturator 22 is removed from tubular member 12. Tubular member 12 then remains employed in abscess ABS and continues to drain pus and other fluidic material therefrom.

As illustrated in FIGS. 5 and 6, a needle member 38 may be removably attached to the distal end of obturator 22, prior to the commencement of an abscess drainage procedure. In that event, another syringe 40 filled with a charge of a local anaesthetic is connected to obturator 22 at the proximal end thereof. Prior to piercing or incising with cutting edge 24 the skin tissues overlying abscess ABS, the surgeon inserts a needle 42 of needle member 38 into the abscess and presses a plunger element 44 of syringe 40 to eject the anaesthetic into the infected tissues. Then, needle member 38 and syringe 40 are removed from obturator 22, syringe 34 being subsequently attached thereto.

As depicted in FIG. 7, another abscess drainage assembly comprises a flexible tubular member 52 provided at a distal end with a ring-shaped lip 54 and further provided in a distal end portion 56 with plurality of perforations in the form of longitudinal slits 58. Distal end portion 56 has a spring bias tending to form a substantially spherical configuration, thereby opening slits 58. A tubular obturator 60 is inserted into tubular member 52 and is provided at a distal end with a cutting edge 62 which projects from tubular member 52. Prior to employment of the abscess drainage assembly illustrated in FIG. 7, tubular member 52 is locked in a stretched cylindrical configuration to obturator 60. To that end, locking component 64 in the form of a pin is inserted through tubular member 52 and obturator tube 60. Also, as described hereinabove with respect to the embodiment of FIG. 2, an annular shoulder (not shown) is provided proximally of cutting edge 62 on obturator 60. Lip 54 on tubular member 52 engages the shoulder to cooperate therewith and with locking pin 64 to maintain tubular member 52 in the stretched cylindrical configuration.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for example, that radio-opaque strip 20 can serve in the guidance of tubular member 12 and obturator 22 during in insertion or employment operation. Thus, abscesses which are located deep inside a patient may be drained by tubular member 12 or 52.

Accordingly, it is to be understood that the drawings and descriptions herein are proferred by way of example to facilitate comprehension of the invention and should not be construed to limit the scope thereof.

What is claimed is:

1. A method for draining an abscess, comprising the steps of:
   providing an obturator inserted inside a tubular member which is at least partially flexible and locked in a stretched configuration to said obturator;
   puncturing a skin surface with a sharp distal end of said obturator;
   inserting a distal end portion of said tubular member and said obturator through said skin surface into an abscess;
   unlocking said obturator from said tubular member by releasing a locking element at a proximal end of said obturator;
   upon completion of said step of unlocking, withdrawing said obturator from said tubular member while maintaining the distal end portion of said tubular member in said abscess; and
   draining fluid from said abscess through said tubular member.

2. The method defined in claim 1 wherein said obturator is provided proximally of a cutting edge with an annular shoulder, said tubular member being provided at its distal end with a ring-shaped lip engaging said shoulder, said step of unlocking including the step of disengaging said lip from said shoulder.

3. The method defined in claim 1 wherein said obturator is rigid, while said tubular member has at least a distal end portion made of a flexible material.

4. The method defined in claim 3 wherein said tubular member has at its distal end a spring bias tending to form said distal end portion into an expanded anchoring configuration, further comprising the step of opening said distal end portion into said expanded anchoring configuration upon inserting said distal end portion of said tubular member through said skin surface into an abscess.

5. The method defined in claim 1 wherein said tubular member is provided in a distal end portion with a plurality of perforations.

6. The method defined in claim 5 wherein said perforations are slits extending longitudinally along said tubular member.

7. The method defined in claim 1 wherein said obturator is tubular, further comprising the step of exerting a suction force on said obturator from a proximal end thereof prior to said step of withdrawing, to obtain a sample of fluidic material in said abscess.

8. The method defined in claim 1, further comprising the step of monitoring the location of said tubular member in said abscess by detecting the location of a radio-opaque strip fastened to said tubular member.

9. An assembly for use in drainage of an abscess, comprising:
   a tubular member having a distal end portion terminating in a distal end, said tubular member having at said distal end a spring bias tending to form said distal end portion of said tubular member into an expanded anchoring configuration, said tubular member having an opening at said distal end;
   an elongate inner member inserted into said tubular member, said inner member having a distal end provided with a cutting edge projecting from said tubular member through said opening; and
   means for releasably locking said inner member to said tubular member to temporarily maintain said tubular member in an essentially cylindrical configuration in opposition to said spring bias, said means for releasably locking including a shoulder provided on said inner member proximally of said cutting edge, said means for releasably locking also including a lip on said tubular member at its distal end, said lip engaging said shoulder.

10. The device defined in claim 9 wherein said inner member is tubular.

11. The assembly defined in claim 10 wherein said inner member has a proximal end, further comprising a syringe connected to said inner member at said proximal end thereof.

12. The assembly defined in claim 9 wherein said inner member has a proximal end, said means for releasably locking including a locking element at said proximal end of said inner member.

13. The assembly defined in claim 9 wherein a radio-opaque strip is fastened to said tubular member.

14. The device defined in claim 9 wherein said expanded anchoring configuration is substantially spherical.

* * * * *